(12) United States Patent
Diodati et al.

(10) Patent No.: US 8,899,267 B2
(45) Date of Patent: Dec. 2, 2014

(54) CONNECTOR ASSEMBLY

(75) Inventors: Anthony Diodati, Mullica Hill, NJ (US); Albert A. Werth, Kewadin, MI (US); Clemens E. Zoellner, Midland, MI (US); Anthony Pagliaro, Landsale, PA (US); Jeffrey D. Chase, Aurora, IL (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 583 days.

(21) Appl. No.: 12/024,811

(22) Filed: Feb. 1, 2008

(65) Prior Publication Data

US 2008/0185056 A1   Aug. 7, 2008

Related U.S. Application Data

(60) Provisional application No. 60/887,751, filed on Feb. 1, 2007.

(51) Int. Cl.
| F16L 37/32 | (2006.01) |
| A61M 39/26 | (2006.01) |
| A61M 39/18 | (2006.01) |
| F16L 37/36 | (2006.01) |
| A61M 39/14 | (2006.01) |
| A61M 39/10 | (2006.01) |

(52) U.S. Cl.
CPC ........ *A61M 39/26* (2013.01); *A61M 2039/1027* (2013.01); *A61M 39/18* (2013.01); *F16L 37/36* (2013.01); *F16L 37/32* (2013.01); *A61M 39/14* (2013.01); *F16L 2201/44* (2013.01)
USPC ................. 137/614.04; 137/614.03

(58) Field of Classification Search
CPC ............ F16L 37/32; F16L 37/35; F16L 37/36
USPC .............. 137/614, 614.04, 614.06, 614.03, 137/614.05; 251/149.1, 149.2; 285/330, 285/331
See application file for complete search history.

(56) References Cited

U.S. PATENT DOCUMENTS 3,837,687 A    9/1974   Leonard
3,865,411 A *  2/1975   Rowe et al. ................... 285/363
(Continued)

FOREIGN PATENT DOCUMENTS

EP    0795342 A    9/1997
EP    0966985 A    12/1999
(Continued)

OTHER PUBLICATIONS

International Search Report from related PCT Application; PCT/US2009/038103; 14 pages.

(Continued)

*Primary Examiner* — Kevin Murphy
(74) *Attorney, Agent, or Firm* — Abel Law Group, LLP; Chi S. Kim

(57) ABSTRACT

A sterile connector assembly for mounting on a fluid system includes a first connector and a second connector. The first connector includes a stem defining a fluid passage therethrough, a first housing surrounding the stem and defining a first aperture, and a first valve disposed over the first aperture. The second connector includes a second housing configured to matingly engage the first housing. The second housing defines a second aperture and defines a seal structure. The seal structure is configured to engage the stem. The second connector also includes a second valve disposed over the second aperture. The second valve is configured to engage the first valve when the first housing engages the second housing.

21 Claims, 10 Drawing Sheets

(56) References Cited

U.S. PATENT DOCUMENTS

| | | | |
|---|---|---|---|
| 3,973,791 A | | 8/1976 | Porta et al. |
| 4,019,512 A | * | 4/1977 | Tenczar ............. 604/411 |
| 4,022,205 A | | 5/1977 | Tenczar |
| 4,030,494 A | | 6/1977 | Tenczar |
| 4,099,748 A | | 7/1978 | Kavick |
| 4,201,208 A | | 5/1980 | Cambio, Jr. |
| 4,256,106 A | | 3/1981 | Shoor |
| 4,277,091 A | | 7/1981 | Hunter |
| 4,280,722 A | | 7/1981 | Guptil et al. |
| 4,285,228 A | | 8/1981 | Gunning |
| 4,330,924 A | | 5/1982 | Kushner et al. |
| 4,334,537 A | | 6/1982 | Peterson |
| 4,334,551 A | | 6/1982 | Pfister |
| 4,371,199 A | | 2/1983 | Kushner et al. |
| 4,418,945 A | | 12/1983 | Kellogg |
| 4,423,732 A | | 1/1984 | Tarjan et al. |
| 4,620,662 A | | 11/1986 | Driggers |
| 4,717,388 A | | 1/1988 | Steer et al. |
| 4,828,160 A | | 5/1989 | Sundholm |
| 4,946,200 A | | 8/1990 | Blenkush et al. |
| 4,991,882 A | * | 2/1991 | Gahwiler ............. 285/331 |
| 4,993,756 A | | 2/1991 | Bechu |
| 5,067,950 A | | 11/1991 | Broadnax, Jr. |
| 5,087,086 A | | 2/1992 | Snedeker |
| 5,122,123 A | | 6/1992 | Vaillancourt |
| 5,131,696 A | | 7/1992 | Sykes et al. |
| 5,380,049 A | | 1/1995 | Smowton |
| 5,393,101 A | | 2/1995 | Matkovich |
| 5,404,632 A | | 4/1995 | Zaborszki |
| 5,492,147 A | | 2/1996 | Challender et al. |
| 5,499,439 A | | 3/1996 | Zaborszki et al. |
| 5,511,720 A | | 4/1996 | Zaborszki et al. |
| 5,535,771 A | | 7/1996 | Purdy et al. |
| 5,638,869 A | | 6/1997 | Zaborszki et al. |
| 5,688,254 A | | 11/1997 | Lopez et al. |
| 5,769,558 A | | 6/1998 | Jekielek |
| 5,788,433 A | | 8/1998 | Grund et al. |
| 5,810,398 A | | 9/1998 | Matkovich |
| 5,931,510 A | | 8/1999 | Mathew et al. |
| 6,022,053 A | | 2/2000 | Hukuda |
| 6,106,027 A | | 8/2000 | Mulvey et al. |
| 6,148,849 A | * | 11/2000 | Green et al. ............. 137/351 |
| 6,193,282 B1 | | 2/2001 | Assenheimer |
| 6,341,802 B1 | | 1/2002 | Matkovich |
| 6,394,506 B1 | | 5/2002 | Street |
| 6,488,320 B1 | | 12/2002 | Anderson |
| 6,536,805 B2 | | 3/2003 | Matkovich |
| 6,604,758 B1 | | 8/2003 | Assenheimer |
| 6,655,655 B1 | | 12/2003 | Matkovich et al. |
| 6,874,522 B2 | * | 4/2005 | Anderson et al. ............. 137/68.3 |
| 6,880,801 B2 | | 4/2005 | Matkovich et al. |
| 7,090,191 B2 | | 8/2006 | Matkovich et al. |
| 7,137,974 B2 | | 11/2006 | Almasian et al. |
| 7,358,505 B2 | | 4/2008 | Woodworth et al. |
| 7,396,051 B2 | | 7/2008 | Baldwin et al. |
| 2002/0093192 A1 | | 7/2002 | Matkovich |
| 2003/0127851 A1 | | 7/2003 | Guslick et al. |
| 2004/0034328 A1 | * | 2/2004 | Unger et al. .................. 604/415 |
| 2004/0251683 A1 | | 12/2004 | Fisher et al. |
| 2005/0015075 A1 | | 1/2005 | Wright et al. |
| 2005/0082826 A1 | * | 4/2005 | Werth ............. 285/243 |
| 2005/0090797 A1 | | 4/2005 | Almasian et al. |
| 2006/0142735 A1 | | 6/2006 | Whitley |
| 2006/0217671 A1 | | 9/2006 | Peppel |
| 2007/0276356 A1 | | 11/2007 | Downing et al. |

FOREIGN PATENT DOCUMENTS

| | | |
|---|---|---|
| EP | 1096193 A2 | 5/2001 |
| EP | 0719970 B1 | 8/2001 |
| EP | 1162399 A2 | 12/2001 |
| EP | 1184613 A2 | 3/2002 |
| EP | 0739469 B1 | 10/2002 |
| EP | 1326044 A2 | 7/2003 |
| JP | 5079192 A | 6/1975 |
| JP | 6-22688 U | 3/1994 |
| JP | 2002514941 A | 5/2002 |
| JP | 2004-195181 A | 7/2004 |
| JP | 2004-222888 A | 8/2004 |
| WO | 90/10816 | 9/1990 |
| WO | 91/02185 | 2/1991 |
| WO | 92/16987 | 10/1992 |
| WO | 9408173 A1 | 4/1994 |
| WO | 9630076 | 10/1996 |
| WO | 98/04468 | 2/1998 |
| WO | 01/14781 A1 | 3/2001 |
| WO | 02/061323 A1 | 8/2002 |
| WO | 2005/019566 A2 | 3/2005 |
| WO | 2005/019718 A1 | 3/2005 |

OTHER PUBLICATIONS

The International Preliminary Report on Patentability for International Application No. PCT/US2008/001426 received from the International Bureau, dated Aug. 13, 2009, 9 pages.

* cited by examiner

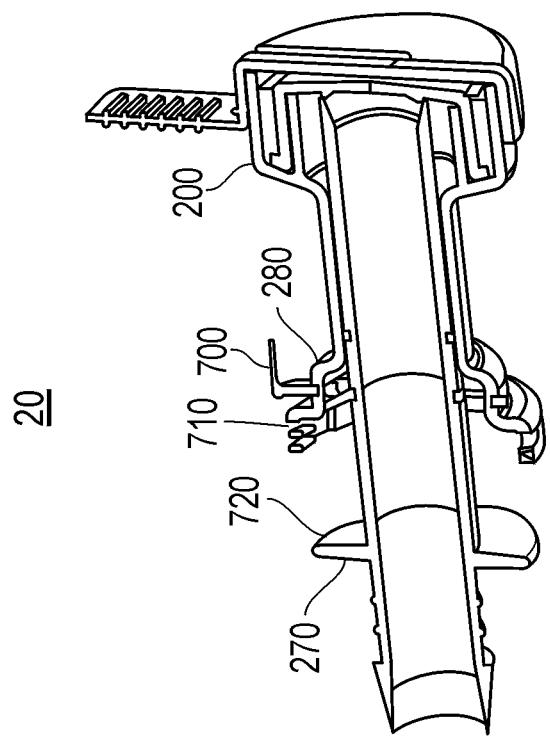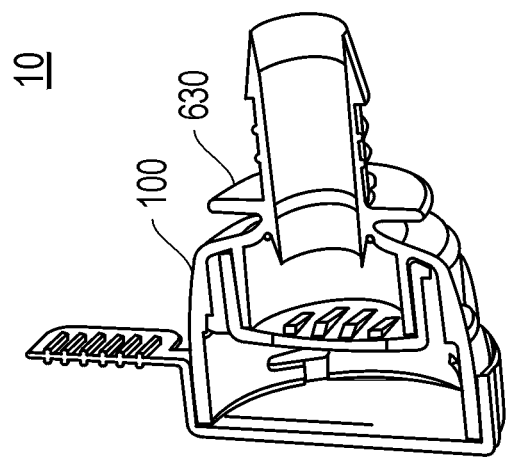
FIG. 7

CONNECTOR ASSEMBLY

CROSS REFERENCE TO RELATED APPLICATIONS

The present application claims priority from U.S. Provisional Patent Application No. 60/887,751, filed Feb. 1, 2007, entitled "CONNECTOR ASSEMBLY", naming inventors Anthony Diodati, Albert A. Werth, Clemens E. Zoellner, Anthony Pagliaro, and Jeffery Chase, which application is incorporated by reference herein in its entirety.

FIELD OF THE DISCLOSURE

This disclosure, in general, relates to a connector assembly. More particularly, the disclosure relates to a sterile connector assembly.

BACKGROUND

Large-scale production of pharmaceuticals, fluids for use in medical applications, and food grade products relies on maintenance of sanitary environments. Exposure of such products to bacteria or contaminants results in a reduced quality and, in some cases, toxic byproducts. As such, food and medical product manufacturers attempt to reduce points of contamination and have turned to sanitary hoses and connectors as part of an effort to maintain a sanitary environment.

In part, manufacturers have turned to connectors with seals. However, typical seals on such connectors are removed just prior to use, resulting in possible exposure of the fluid to the ambient environment. Manufacturers have also attempted to use seals that can be punctured so that removal prior to use is unnecessary. However, the design of such seals introduces the seals within the fluid path. As such, improved connectors would be desirable.

SUMMARY

In a particular embodiment, a connector includes a stem defining a fluid passage therethrough, a housing surrounding the stem and defining an aperture, and a valve disposed over the aperture. The stem is configured to matingly engage a complimentary structure located on a complimentary connector. The housing is configured to engage a complimentary housing of the complimentary connector. The valve is configured to align with a complimentary valve when the housing engages the complimentary housing.

In another exemplary embodiment, a connector includes a first housing defining an aperture configured to engage a complimentary second housing of a complimentary connector, a first valve disposed over the aperture, and a seal structure configured to engage a stem of the complimentary connector after the first and second housings engage. The first valve is configured to align with a complimentary second valve when the first housing engages the second housing.

In a further exemplary embodiment, a sterile connector assembly for mounting on a fluid system includes a first connector and a second connector. The first connector includes a stem defining a fluid passage therethrough, a first housing surrounding the stem and defining a first aperture, and a first valve disposed over the first aperture. The second connector includes a second housing configured to matingly engage the first housing. The second housing defines a second aperture and defines a seal structure. The seal structure is configured to engage the stem. The second connector also includes a second valve disposed over the second aperture. The second valve is configured to engage the first valve when the first housing engages the second housing.

In an additional example, a fluid system includes a first fluid container coupled to a distal end of a first housing of a first connector. The proximal end of the first housing defines a first aperture. A first valve is disposed over the first aperture. The proximal end further defines a seal structure. The fluid system also includes a second fluid container coupled to a stem of a second connector. The second connector includes the stem and a second housing. A proximal end of the second housing is configured to matingly engage the first housing. The stem defines a fluid passage therethrough. The second housing surrounds the stem and defines a second aperture. A second valve is disposed over the second aperture. The second valve is configured to align with the first valve when the first housing engages the second housing. The stem is configured to engage the seal structure of the first housing after the first and second housings engage.

BRIEF DESCRIPTION OF THE DRAWINGS

The present disclosure may be better understood, and its numerous features and advantages made apparent to those skilled in the art by referencing the accompanying drawings.

FIGS. 1, 2, 3, 4, 5, 6 and 7 include illustrations of an exemplary connector.

The use of the same reference symbols in different drawings indicates similar or identical items.

DETAILED DESCRIPTION OF THE DRAWINGS

Figure 1:
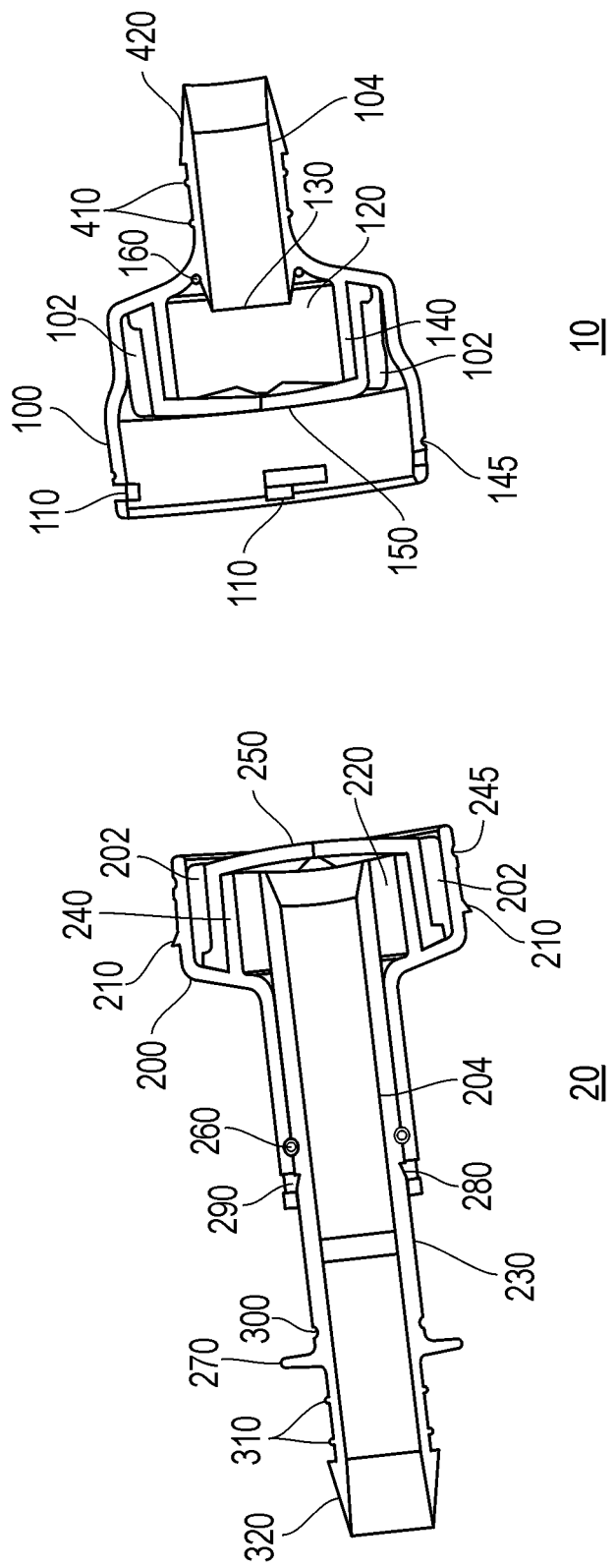

In an exemplary embodiment, a connector includes mating connectors that can be coupled together and to various fluid conduit systems to provide a fluid path between the fluid systems. The connector assembly provides a sterile environment for fluid to flow between containers or conduits and prevents contaminants from entering the fluid path.

In an embodiment illustrated in FIGS. 1, 2, 3, 4, and 5 the connector assembly includes two connectors 10 and 20. The first connector including a housing 100 that defines a seal structure 130 and a coupling 420. The second connector 20 includes a housing 200 surrounding a stem 230. In an example, the stem 230 is configured to move axially relative to the housing 200. The stem 230 may include a coupling 320. When the first connector 10 and the second connector 20 are coupled, the first and second housings (100 and 200) are configured to lock together and the stem 230 is configured to engage the seal structure 130 to define a fluid passage through the coupling assembly. For directional orientation, each connector (10 and 20) and their associated housings (100 and 200) have a proximal end illustrated nearest the opposing connector and a distal end illustrated furthest from the opposing connector. The proximal ends of the first housing 100 and second housing 200 are dimensioned to matingly engage. In an embodiment, the first housing 100 has an inside diameter and the second housing 200 has an outside diameter wherein the inside diameter of the first housing 100 is greater than the outside diameter of the second housing 200 to provide a frictional fit. In an alternative embodiment, the first housing 100 has an outside diameter and the second housing 200 has an inside diameter wherein the inside diameter of the second housing 200 is greater than the outside diameter of the first housing 100 to provide a frictional fit.

In an embodiment, the first housing 100 and the second housing 200 may include an interlocking mechanism adapted to interlock the first housing 100 in a predetermined relationship with the second housing 200. In an example, the interlocking mechanism may have any suitable configuration to prevent the axial movement of first housing 100 and second housing 200 when they are matingly engaged. The interlocking mechanism may also be configured to prevent rotational movement of first housing 100 and second housing 200 when they are matingly engaged. Exemplary interlocking mechanisms include threaded connections or tab and groove connections. In an example, as illustrated in FIG. 1, the first housing 100 includes an inner sidewall with a groove 110 along at least a portion of the circumference of the sidewall. One or more grooves 110 may extend along the inner sidewall. The opposing second housing 200 includes an outer diameter. The outer diameter of the second housing 200 includes one or more tabs 210 that extend beyond the periphery of the outside diameter. Hence, when the second housing 200 and first housing 100 are matingly engaged, the tabs 210 of the second housing 200 engage the grooves 110 of the first housing 100 to interlock the housings 100, 200. For example, tabs 210 are configured to bend with the frictional force of the sidewall of first housing 100 and grooves 110. In an exemplary embodiment, the grooves 110 are configured such that first housing 100 and second housing 200 are rotated to engage the tabs 210 with the grooves 110 and lock the housings 100 and 200. For example, the groove 110 may be configured in an "L" shape to first proximally and axially guide the tab 210 and next rotationally guide the tab with first housing 100. In an embodiment, the interlocking device is arranged to irreversibly lock when engaged, i.e., the unlocking would result in damage to the housing (100 or 200).

In an embodiment, the first housing 100 includes a valve support system 140 that defines a first aperture 120 or internal chamber with an open proximal end. Further, the second housing 200 includes a valve support system 240 that defines a second aperture 220 or internal chamber with an open proximal end. Typically, the first aperture 120 and the second aperture 220 are configured to align, such as aligning in a concentric fashion along an axis, when the first housing 100 is coupled to the second housing 200. As illustrated, the valve support systems 140 and 240 are integrally formed within the housings 100 and 200, respectively. Alternatively, the valve support systems 140 and 240 may be formed as separate pieces and fixed within the housings 100 and 200, respectively.

In an embodiment, the stem 230 and the seal structure 130 matingly engage with a frictional fit. Alternatively, the connector 10 may include an axially movable stem and the connector 20 may include a seal structure. In a further example, both connectors 10 and 20 may include axially movable stems. In a particular embodiment, the stem 230 and seal structure 130, when engaged, define a generally hollow body having an interior surface, defining a lumen for fluid flow therethrough to connect the distal ends of connectors 10 and 20, such as a fluid passage between the couplings 420 and 320.

In an exemplary embodiment, a valve 150 seals the open proximal end of the first aperture 120 defined by the first housing 100. The valve 150 is affixed to prevent inadvertent displacement of the valve 150 and exposure of the first aperture 120 to the ambient environment. For example, the valve 150 may be attached to a valve support system 140 defining the first aperture 120 through any suitable technique to physically or chemically attach the valve 150. In an exemplary embodiment, the valve 150 is permanently affixed to the valve support system 140. In an embodiment, the valve 150 is permanent affixed with a valve retainer 102. The valve retainer 102 may be dimensioned between the valve 150 and the inside diameter of the housing 100 in any suitable configuration to permanently affix the valve 150 to the valve support system 140. For instance, the valve retainer 102 may be dimensioned to frictionally fit the valve 150 to the valve support system 140.

In addition, a valve 250 may seal the open proximal end of the second aperture 220 in the second housing 200. The valve 250 may be affixed to prevent inadvertent displacement of the valve 250 and exposure of the second aperture 220 to the ambient environment. The valve 250 may be attached to a valve support system 240 defining the second aperture 220 through any suitable technique to physically or chemically attach valve 250. The valve 250 may be permanently affixed to the valve support system 240. In an embodiment, the valve 250 is permanent affixed with a valve retainer 202. The valve retainer 202 may be dimensioned between the valve 250 and the inside diameter of the housing 200 in any suitable configuration to permanently affix the valve 250 to the valve support system 240. For instance, the valve retainer 202 may be dimensioned to frictionally fit the valve 250 to the valve support system 240.

Figure 2:
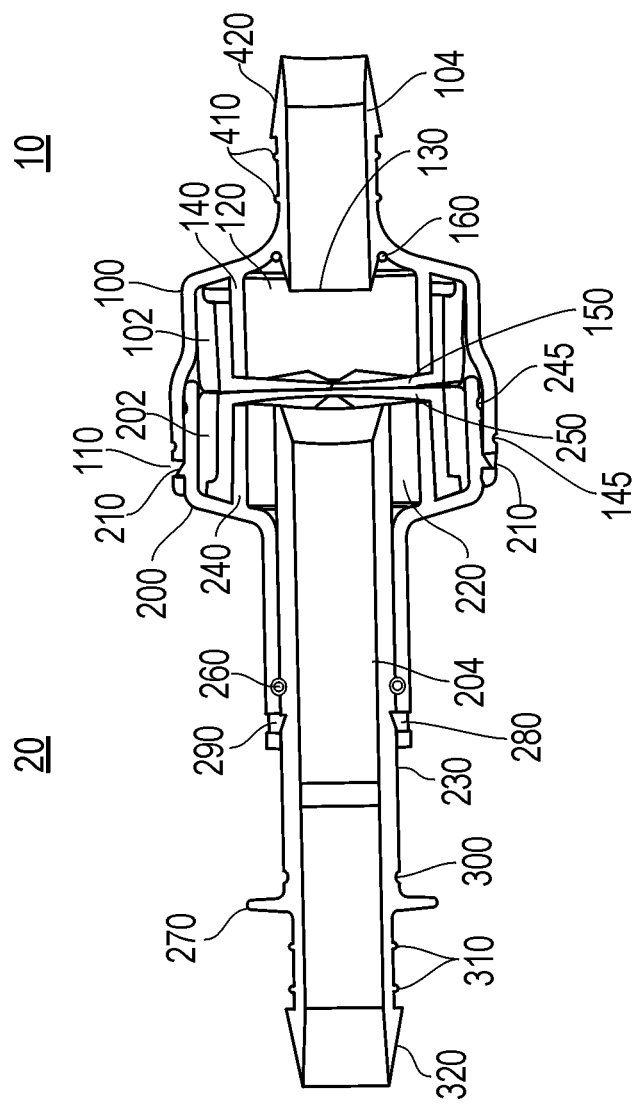

In an embodiment, the valve 150 is configured to align with valve 250. For example, the housings 100 and 200 may be dimensioned such that when the first housing 100 and the second housing 200 matingly engage, valve 150 aligns with and contacts valve 250, as illustrated in FIG. 2. In an exemplary embodiment, valve 150 engages or may adhere to valve 250. The valves 150 and 250 may have a dome-shaped configuration where the convex portion extends toward the proximal end of the second aperture 220 and the first aperture 120, respectively to facilitate face-to-face engagement of the valves 150 and 250.

In an embodiment, the stem 230 is movably housed in the second housing 200. For example, the stem 230 is dimensioned to move axially within the second housing 200 and proximally to engage the seal structure 130 in first housing 100. In an example, the distal end of the stem 230 includes a flange 270 on the outside diameter of the stem 230. Typically, once the valves 150 and 250 are aligned, the stem 230 is engaged to move axially and proximally through the valve 250 and the valve 150 to fold both valves in the direction of the movement of the stem 230 and to the outside diameter of the stem 230 until the stem 230 engages the seal structure 130. In an exemplary embodiment, the stem 230 engages seal 160 on the proximal end of the seal structure 130 to provide a tight frictional fit.

In a further embodiment, the stem 230 may include a locking mechanism. The locking mechanism may be of a configuration that restricts the axial retreat of the stem 230 within the second housing 200. The second housing 200 is typically dimensioned to allow axial advancement of the stem 230 and maintain a tight frictional fit with seal structure 130. In an exemplary embodiment, once seal 160 is engaged with stem 230, the locking mechanism may prevent axial movement of the stem 230 in the distal direction relative to the second housing 200. For example, a locking tab 290 may be located on the inside diameter of the distal end of the housing 200. In an example, the locking tab 290 may be a radially projecting fine. Further, one or more grooves 280, 300 may be located on the outside diameter of stem 230 and may be configured to engage the locking tab 290. The first groove 280 may be configured along the central axis of stem 230 to prevent movement of the stem 230 in the distal direction relative to the housing 200 and accidental exposure of the aperture 220 to the environment prior to engaging first housing 100. Once first housing 100 and second housing 200 are engaged, the flange 270 is moved proximally until second groove 300 is engaged with locking tab 290. The second groove 300 may be configured along the distal axis of stem 230 to prevent further axial movement once stem 230 is engaged with seal 160, such as to prevent the stem 230 from disengaging the seal 160. In an embodiment, the locking mechanism irreversibly locks when engaged.

The stem 230 may include an interlocking mechanism that is configured to pass through the housing 200 to engage stem 230. As illustrated in the embodiments of FIGS. 6, 7, 8, 9, and 10 the interlocking mechanism includes a clip 700. Clip 700 may be shaped in a horseshoe configuration with a forked end 810 and a closed end 820. The closed end 820 is typically configured for the user to engage the interlocking mechanism and may be dimensioned with a flat face. In an embodiment, the interior of forked end 810 includes elongated tabs 830. The forked end 810 may further include hooks 840. Elongated tabs 830 can engage the first groove 280 located on the outside diameter of the stem 230. Once the first housing 100 and the second housing 200 are engaged, the closed end 820 is pushed toward the housing 200 to disengage the elongated tabs 830 from the first groove 280. The hooks 840 may be dimensioned to engage the outside diameter of the housing 200 to lock the clip 700 in an open position. The clip 700 is dimensioned to allow proximal movement of the stem 230 once the hooks 840 engage the outside diameter of the housing 200. In an embodiment, the locking mechanism irreversibly locks when engaged.

Figure 12:
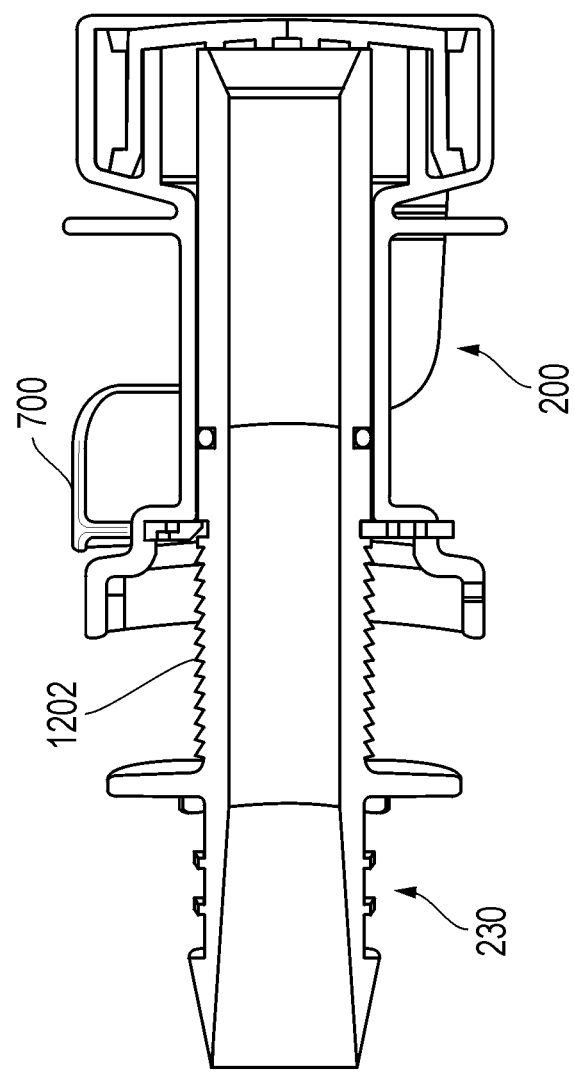
FIG. 12 includes an illustration of an exemplary connector.

In a further example, the stem 230 may include a set of adjacent ridges 1202, as illustrated in FIG. 12. For example, the adjacent ridges 1202 may be concentric ridges to engage the housing 200 or the clip 700. In particular, the adjacent ridges 1202 and the housing 200 or the clip 700 engage to permit the stem 230 to ratchet forward, preventing backward or reverse movement of the stem 230.

In a further embodiment, one or more locking tabs 720 may be configured along the outside diameter of the flange 270. The distal end of the housing 200 may be configured to engage the flange 270 and the locking tab 720. For instance, the inside diameter of the distal end of the housing 200 may be greater than the outside diameter of the flange 270 to enable the flange 270 to matingly engage the distal end of the housing 200. Further, the distal end of the housing 200 may include complimentary grooves 710 to matingly engage the tabs 720 of the flange 270 to interlock the flange 270 and the housing 200. For example, the tabs 720 are configured to bend with the frictional force of the sidewall of the second housing 200 and the grooves 710. In an exemplary embodiment, the grooves 710 are configured such that the flange 270 and the second housing 200 are rotated to engage the tabs 720 with the grooves 710 and lock the flange 270 and the housing 200. For example, the groove 710 may be configured in an "L" shape to first proximally and axially guide the tab 720 and next rotationally guide the tab with the second housing 200. The groove 710 and the tab 720 may be configured to prevent further axial movement once the stem 230 is engaged with the seal 160, such as to prevent the stem 230 from disengaging the seal 160. In an embodiment, the locking mechanism irreversibly locks when engaged.

To provide a conduit for fluid flow, the stem 230 and the seal structure 130 may slidingly engage after pushing open the valves 150 and 250. In an embodiment, the engaged valves 150 and 250 are configured to fold toward the distal end of first housing 100 along the outside diameter of the second stem 230, for example, in the direction of the movement of the stem 230. The valves 150 and 250 and the apertures 120 and 220 are dimensioned such that any fluid flow is prevented from contacting the valves 150 and 250, maintaining a sterile environment.

The integrity of the sterile environment may be maintained through the stem 230 contacting the seal structure 130, while not being exposed to the environment beyond the sealed apertures 120 and 220. In particular, the stem 230 is configured to move through the valves 150 and 250 without contacting an outside surface of the valves 150 and 250. In an embodiment, the connector 10 includes the seal structure 130 and a seal 160 around the proximal end of the seal structure 130. The seal structure 130 is configured to engage the proximal end of stem 230 after the first and second housings 100 and 200 engage. For instance, the proximal end of the stem 230 is dimensioned to form a tight frictional fit between the seal structure 130 and the stem 230 when the stem 230 is matingly engaged with seal structure 130 and engages seal 160. In an example, the seal 160 may be continuous and may completely engage the proximal end of the stem 230. For example, the seal 160 may be an O-ring.

In an embodiment, the stem 230 is surrounded by the housing 200. The stem 230 is dimensioned to form a tight frictional fit between the outside diameter and distal end of the stem 230 and the distal end of the housing 200. In addition, a seal 260 is located between the housing 200 and the stem 230. For example, the seal 260 may continuously surround the circumference of the stem 230. In an example, the seal 260 may be disposed in a groove in the outside diameter of the stem 230. Alternatively, the seal 260 may be disposed in a groove along an inside surface of the distal end of the housing 200. In an example, the seal 260 may be an O-ring. In a particular embodiment, the seal 260 forms a seal with the stem 230 and the interior, distal end of housing 200 to seal the second aperture 220 from the ambient environment and allow the stem 230 to move axially.

Typically, the valves 150 and 250 and the seals 160 and 260 may be formed of any suitable material, which precludes the passage of contaminants. In an embodiment, the valves 150 and 250 and the seals 160 and 260 may be made of any material approved by the FDA for fluid transport. In an exemplary embodiment, the valves 150 and 250 and the seals 160 and 260 may be formed of a polymeric material. An example polymeric material includes an elastomer, such as a silicone elastomer, thermoplastic elastomer, thermoplastic vulcanizate, or polymer containing ethylene propylene diene monomer. The valves 150 and 250 and the seals 160 and 260 may also be treated with an antibacterial compound or contain an antibacterial layer.

Figure 5:
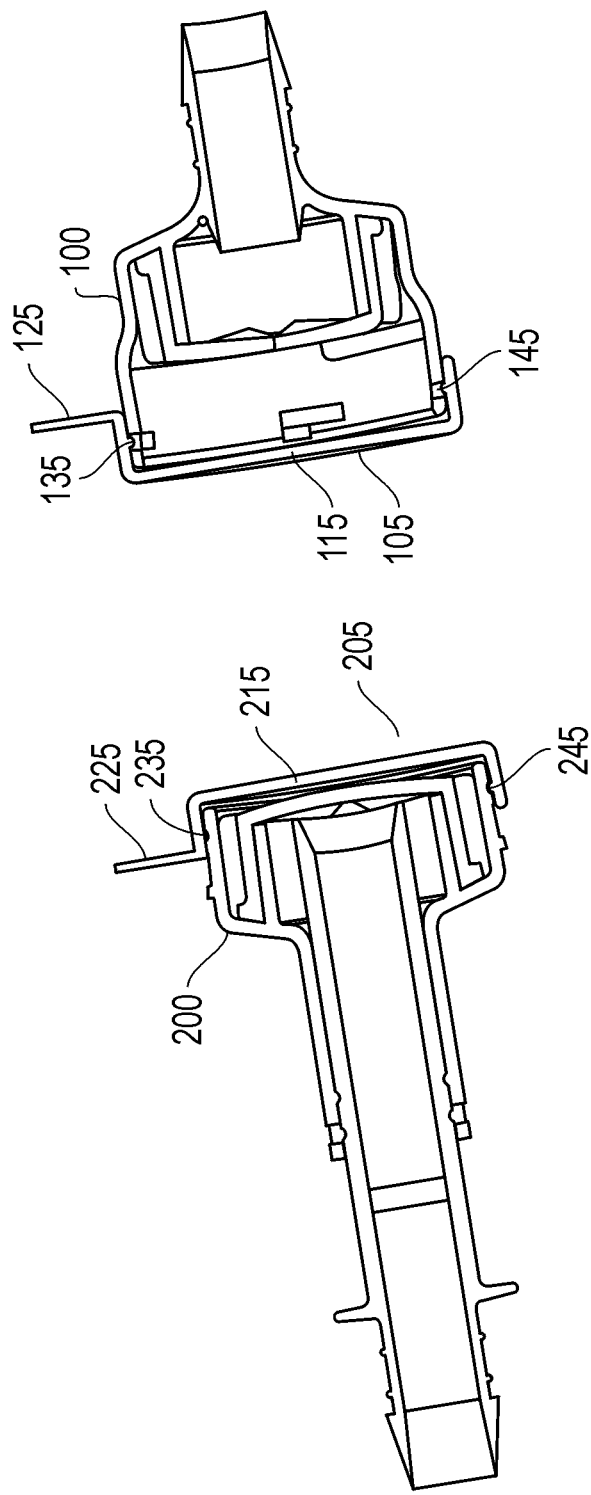

In an embodiment, the proximal end of the housings 100 and 200 may include a cap (105 or 205, respectively) to maintain a sterile environment within the housing as well as protect the valves 150 and 250 from environmental contaminants, as illustrated in FIG. 5. Typically, the caps 105 and 205 may be easily removed prior to coupling the housings 100 and 200. As illustrated in FIG. 5, the caps 105 and 205 may include a cover 115 and 215 and a plurality of ribs 135 and 235. Typically, the proximal ends of the housings 100 and 200 include a sidewall on the outside diameter of the housings 100 and 200 with an annular groove 145 and 245. When the caps 105 and 205 are mounted to the proximal end of the housings 100 and 200, the ribs 135 and 235 engage the annular grooves 145 and 245 to securely hold the caps 105 and 205. In an embodiment, the caps 105 and 205 are dimensioned to fully contain the interior of the housings 100 and 200. The sidewalls of the housings 100 and 200 are dimensioned so that the caps 105 and 205 do not engage the valves 150 and 250. The caps 105 and 205 may further include a tab 125 and 225 attached to the covers 115 and 215 so the caps 105 and 205 can be easily removed.

Figure 6:
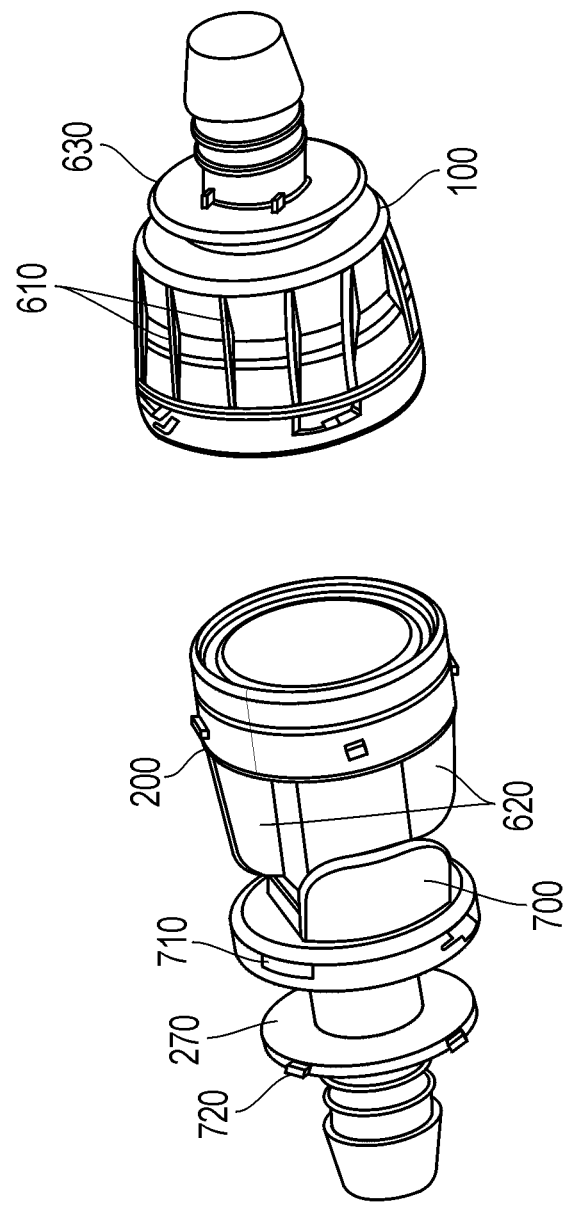

In an embodiment, the housing 100 or 200 may be configured to facilitate gripping of the housing by the user. Particularly, the housing 100 or 200 may be configured so the user can easily engage the housing 100 or 200. For instance, the outside surface of the housing 100 or 200 may have roughened, textured, or raised features. As illustrated in FIG. 6, the housing 100 may contain a plurality of ridges 610 along at least a portion of the outside surface of the housing 100. The housing 100 may also contain a flange 630. In another exemplary embodiment, the housing 200 includes a plurality of wings 620 along the outside surface of the stem portion of the housing 200.

The connector assembly may be made of any material that is compatible with the nature of the particular fluid or sterilization technique utilized. In an embodiment, at least a portion of the connector assembly, such as the housings 100 and 200 and the caps 105 and 205 are made of any material approved by the FDA for fluid transport, such as USP ADCF (animal derived component free) materials and USP Class VI/ADCF materials. In an exemplary embodiment, the materials may be polyvinylidene fluoride and polypropylene. Further, the housing may include independent, multiple components or continuous, integral components.

In an exemplary embodiment, the stem 230 has an interior surface and an exterior surface. Further, the housing 100 defining the seal structure 130 may also have an interior and an exterior surface. The interior surface, for example, defines a lumen for fluid flow therethrough. In general, the interior surface has an initial roughness (Ra) not greater than 50 microns, such as not greater than about 10 microns, or even, not greater than about 1 micron. An exemplary polymer for use in the stems, seals, and other components includes a polyolefin. In an example, the polyolefin includes polyethylene or polypropylene. In particular, the polyolefin may include halogenated polyolefin. For example, the halogenated polyolefin may include polyvinyl chloride (PVC), polyvinyl fluoride (PVF), polyvinylidene fluoride (PVDF), polyvinylidene chloride (PVDC), polycholorotrifluoroethylene (PCTFE), polytetrafluoroethylene (PTFE), or blends or copolymers thereof. In a particular embodiment, the liner 104, 204 is formed of a perfluoronated polymer, such as PTFE. In a particular embodiment, a fluoropolymer may be selected from those sold under the Chemfluor® trademark, available from Saint Gobain Performance Plastics Corporation. In another example, the material may include silicone. In a further example, the material may be elastomeric.

The distal end of each housing 100 and 200 may be configured to engage a fluid system, such as a section of tubing. For example, the outside diameter of the distal end of the stem 230 the housing 100 opposite the seal structure 130 may include at least one annular rib 310, 410 to engage a section of tubing. The distal end of the stem 230 and the housing 100 may further include a tapered outside diameter to define couplings 320, 420 to provide axial guidance for tubing and a tight frictional fit to provide a seal between the inside diameter of the tubing and the outside diameter of the distal end of the stem 230 and of the housing 100. Alternatively, the stem 230 and the housing 100 may be configured with couplings of other types, such as those coupling configurations known in the industry. In an embodiment, the distal end of the first housing 100 and the stem 230 are configured with an outside diameter of about ¼ inch, about ⅜ inch, and about ½ inch.

Figure 11:
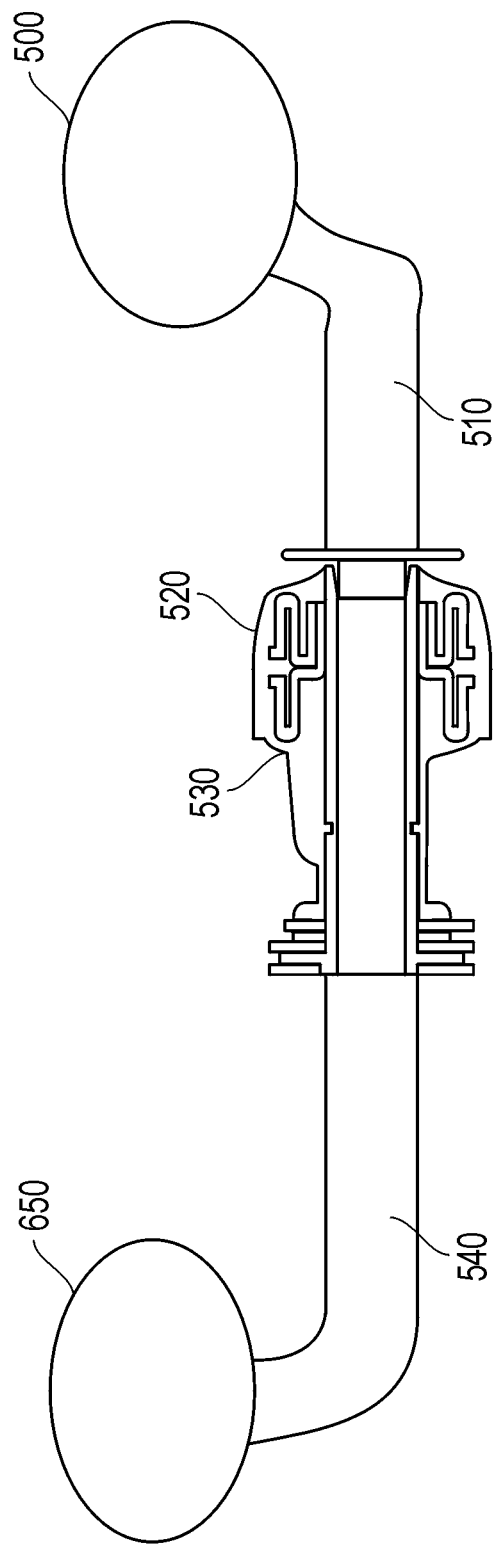
FIG. 11 includes an illustration of an exemplary assembly including an exemplary connector.

Each connector may be attached to or may be formed as part of any suitable fluid container or conduit, for example, a section of tubing, an inlet or outlet of a housing, such as a filter housing or drip chamber housing, or a flexible bag such as a blood bag. FIG. 11 includes an illustration of an exemplary fluid system in which a container 500 is fluidically coupled to a container 650 through a tubing 510 coupled to a first connector 520 that is coupled to a second connector 530, which is coupled to a tubing 540 that is coupled to the container 650. In particular, the connector may be suitable for fluid communication where the pressure rating is greater than or equal to about 50 psi or 3.5 bar.

In an exemplary embodiment, the connector assembly is suitable for sterilization. In an embodiment, the connector may be sterilized by radiation sterilization or heat sterilization. In particular, the materials of the connector may be selected based on the anticipated method of sterilization. Particularly, the connector assembly may be configured for sterilization in an autoclave at temperatures of about 134° C. at 17 psi for about 1 hour. Alternatively, the connector assembly may be configured for sterilization by radiation using gamma rays at 25 kGy for 2 doses. Further, the connector assembly may be packaged to maintain sterilization.

Figure 3:
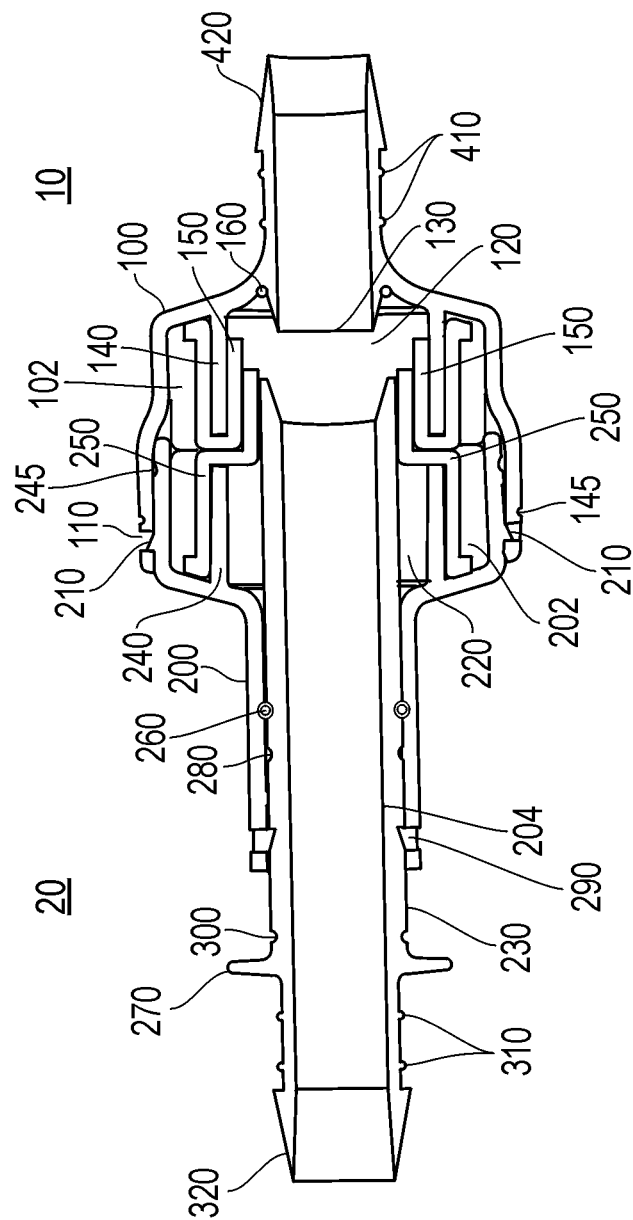
Figure 4:
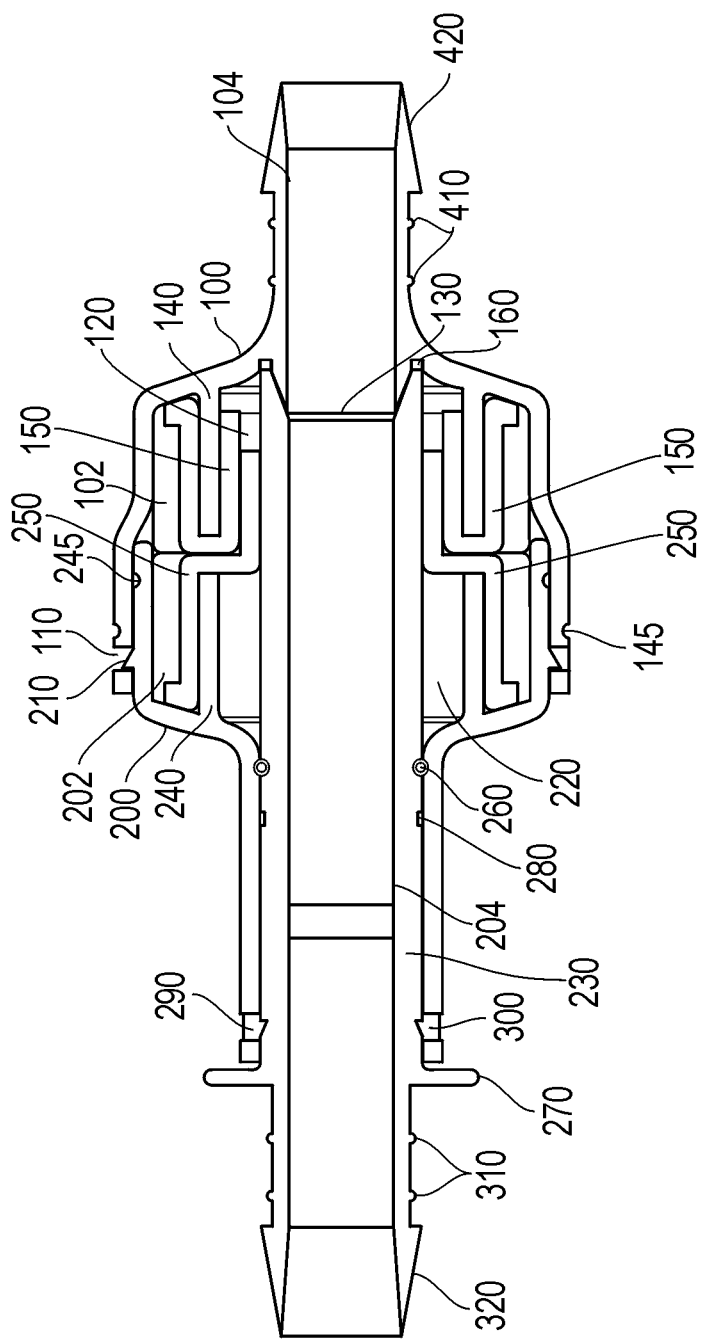

In an exemplary embodiment, operation of the connectors includes removing the caps 105 and 205 from the first housing 100 and the second housing 200, respectively. The operator then matingly engages the first housing 100 and the second housing 200, as illustrated in FIG. 2. The interlocking tab 210 of the second housing 200 engages the groove 110 of the first housing 100 axially and proximally and the housings 100 and 200 are rotated and permanently locked. When the housings 100 and 200 are pushed together, the valves 150 and 250 engage and seal to one another. An operator may push the flange 270 to axially and proximally move the stem 230. The stem 230 may open the path for fluid to flow through by pushing open the valves 150 and 250 in the direction of the movement of the stem 230 and to the outside diameter of the stem 230, as illustrated in FIG. 3. The flange 270 is pushed until it engages the seal 160 of the seal structure 130, the stem 230 is locked into position by the tab 290 and the second groove 300, and the stem 230 is sealed with the seal 260, as illustrated in FIG. 4. The sanitary and sterile connection is complete.

Figure 9:
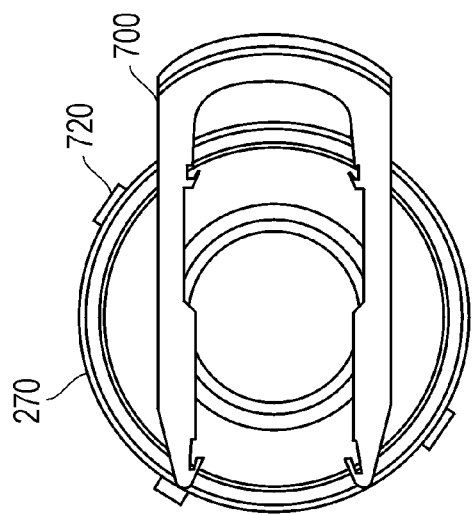
FIGS. 8, 9, and 10 include illustrations of an exemplary interlocking mechanism.
Figure 10:
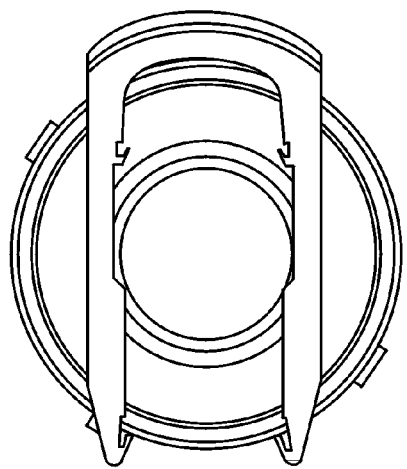
Figure 8:
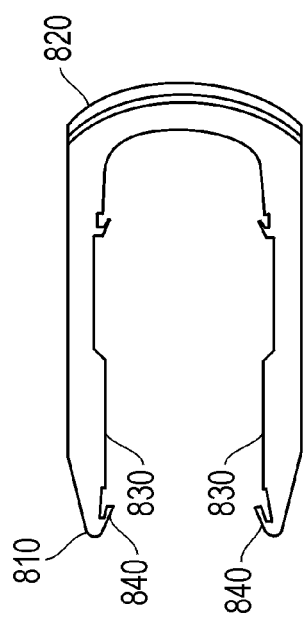

In another exemplary embodiment, operation of the operation of the connectors includes removing the caps 105 and 205 from the first housing 100 and the second housing 200, respectively. The operator then matingly engages the first housing 100 and the second housing 200. The interlocking tab 210 of the second housing 200 engages the groove 110 of the first housing 100 axially and proximally and the housings 100 and 200 are rotated and permanently locked. When the housings 100 and 200 are pushed together, the valves 150 and 250 engage and seal to one another. As illustrated in FIGS. 9 and 10, an operator may push the clip 700 to unlock the stem 230 from the groove 280. The operator may push the flange 270 to axially and proximally move the stem 230. The stem 230 may open the path for fluid to flow through by pushing open valves 150 and 250 in the direction of the movement of the stem 230 and to the outside diameter of the stem 230. The flange 270 is pushed until the stem 230 engages the seal 160 of the seal structure 130. The Stem 230 is locked into position by rotating and permanently locking the tab 720 and the groove 710, and the stem 230 is sealed with seal 260. The sanitary and sterile connection is complete.

In particular, the connector assembly and method of connecting the assembly may provide advantages over other sterile connectors. For example, the integrity of the sterile environment may be maintained through the stem 230 contacting the seal structure 130 while not being exposed to the environment beyond the sealed apertures 120 and 220. In particular, the stem 230 is configured to move through the valves 150 and 250 without contacting an outside surface of the valves 150 and 250.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A connector comprising:
    a stem defining a fluid passage therethrough having a proximal end, a distal end, and a uniform length therebetween, wherein the proximal end of the stem includes an internal chamber with an open end and is configured to matingly engage a complimentary seal structure having a seal located on an outside diameter of a fluid passage on a complimentary connector;
    a housing surrounding the stem and defining an aperture, wherein the housing is configured to engage a complimentary housing of the complimentary connector; and
    a valve disposed over the aperture, wherein a majority of an innermost surface area of an external surface of the valve is configured to align with and seal to a majority of an innermost surface area of an external surface of a complimentary valve when the housing engages the complimentary housing, and wherein the stem is configured to move in relation to the housing and open a path for a fluid to flow between a distal end of the connector positioned furthest from the complimentary connector and a distal end of the complimentary connector positioned furthest from the connector by uniformly engaging the valve to fold open the valve and complimentary valve.

2. The connector of claim 1, wherein the stem is configured to move in relation to the housing and through the valve and complimentary valve to engage the complimentary seal structure after the housing engages the complimentary housing.

3. The connector of claim 2, wherein the valve is configured to fold with the complimentary valve in a direction of movement of the stem when the stem moves through the valve and the complimentary valve.

4. The connector of claim 1, wherein the valve comprises a silicone elastomer, an ethylene propylene diene monomer (EPDM), a thermoplastic elastomer (TPE), or a thermoplastic vulcanizate (TPV).

5. The connector of claim 1, wherein the housing further includes a proximal end and a cap disposed thereon.

6. The connector of claim 1, wherein the stem further includes an interior surface wherein the interior surface defines the fluid passage.

7. The connector of claim 6, wherein the interior surface comprises a halogenated polyolefin.

8. The connector of claim 1, wherein the housing includes an interlocking mechanism configured to matingly engage the complimentary housing.

9. The connector of claim 1, wherein the housing includes at least one tab; and the stem includes at least one groove, wherein the at least one tab and the at least one groove are configured to matingly engage.

10. The connector of claim 1, wherein the at least one seal includes an O-ring.

11. The connector of claim 1, wherein at least a portion of the housing comprises polyvinylidene fluoride or polypropylene.

12. The connector of claim 1, wherein the stem further includes a flange.

13. The connector of claim 12, wherein the flange is configured to abut the housing when the stem engages the complimentary seal structure.

14. A connector comprising:
    a first housing defining an aperture configured to engage a complimentary second housing of a complimentary connector;
    a first valve disposed over the aperture, wherein a majority of an innermost surface area of an external surface of the first valve is configured to align with and seal to a majority of an innermost surface area of an external surface of a complimentary second valve when the first housing engages the second housing; and
    a seal structure having a seal located on an outside diameter of a fluid passage, the seal structure configured to engage a proximal end of a stem of the complimentary connector after the first and second housings engage, wherein the stem has an internal chamber with an open end on the proximal end, a distal end, and a uniform length therebetween, and wherein the stem is configured to move in relation to the second housing and open a path for a fluid to flow between a distal end of the connector positioned furthest from the complimentary connector and a distal end of the complimentary connector positioned furthest from the connector by uniformly engaging the second valve to fold open the first valve and the second valve.

15. The connector of claim 14, wherein the stem of the complimentary connector is configured to move through the first and second valves to engage the seal structure.

16. The connector of claim 15, wherein the first valve is configured to fold with the second valve in a direction of the movement of the stem when the stem moves through the first and second valves.

17. The connector of claim 14, wherein the seal structure includes an O-ring.

18. A sterile connector assembly for mounting on a fluid system comprising:
   a first connector including:
      a stem having an internal chamber with an open end on a proximal end, a distal end, and a uniform length therebetween defining a fluid passage therethrough;
      a first housing surrounding the stem and defining a first aperture; and
      a first valve disposed over the first aperture; and
   a second connector including:
      a second housing configured to matingly engage the first housing, the second housing defining a second aperture and defining a seal structure having a seal located on an outside diameter of a fluid passage, wherein the seal structure is configured to engage the proximal end of the stem; and
      a second valve disposed over the second aperture, wherein a majority of an innermost surface area of an external surface of the second valve is configured to engage with and seal to a majority of an innermost surface area of an external surface of the first valve when the first housing engages the second housing, wherein the stem is configured to move in relation to the first housing and open a path for a fluid to flow between a distal end of the first connector positioned furthest from the second connector and a distal end of the second connector positioned furthest from the first connector by uniformly engaging the first valve to fold open the first valve and the second valve.

19. The sterile connector assembly of claim 18, having a pressure rating of at least about 50 psi.

20. A fluid system comprising:
   a first fluid container coupled to a distal end of a first housing of a first connector, wherein a proximal end of the first housing defines a first aperture, a first valve disposed over the first aperture, and wherein the proximal end further defines a seal structure having a seal located on an outside diameter of a fluid passage, wherein the seal structure is configured to engage a proximal end of a stem of a second connector; and
   a second fluid container coupled to a distal end of the stem of the second connector, the second connector including the stem and a second housing, a proximal end of the second housing configured to matingly engage the first housing; the stem having an internal chamber with an open end on the proximal end and a uniform length therebetween the proximal end and the distal end defining a fluid passage therethrough, the second housing surrounding the stem and defining a second aperture, a second valve disposed over the second aperture, wherein a majority of an innermost surface area of an external surface of the second valve is configured to align with and seal to a majority of an innermost surface area of an external surface of the first valve when the first housing engages the second housing, and wherein the stem is configured to move in relation to the second housing and open a path for a fluid to flow between a distal end of the first connector positioned furthest from the second connector and a distal end of the second connector positioned furthest from the first connector by uniformly engaging the second valve to fold open the first valve and the second valve, and wherein the stem is further configured to engage the seal structure of the first housing after the first and second housings engage.

21. The fluid system of claim 20, wherein the distal end of the first housing and a distal end of the second housing have an outside diameter of about ¼ inch, about ⅜ inch, or about ½ inch.

\* \* \* \* \*